US009375468B2

(12) United States Patent
Adlerberth et al.

(10) Patent No.: US 9,375,468 B2
(45) Date of Patent: Jun. 28, 2016

(54) PREVENTION OF INFLAMMATORY DISORDERS IN DOMESTIC NON-HUMAN MAMMALS

(71) Applicant: Premune AB, Stockholm (SE)

(72) Inventors: Ingegerd Adlerberth, Göteborg (SE); Anna Rudin, Göteborg (SE); Agnes Wold, Göteborg (SE)

(73) Assignee: Premune AB, Stockholm (SE)

( * ) Notice: Subject to any disclaimer, the term of this patent is extended or adjusted under 35 U.S.C. 154(b) by 0 days.

(21) Appl. No.: 14/377,450

(22) PCT Filed: Feb. 5, 2013

(86) PCT No.: PCT/SE2013/050094
§ 371 (c)(1),
(2) Date: Aug. 7, 2014

(87) PCT Pub. No.: WO2013/119170
PCT Pub. Date: Aug. 15, 2013

(65) Prior Publication Data
US 2015/0079131 A1    Mar. 19, 2015

(30) Foreign Application Priority Data

Feb. 8, 2012    (SE) .................................. 1250090

(51) Int. Cl.
| | | |
|---|---|---|
| A61K 39/00 | (2006.01) | |
| A61K 39/02 | (2006.01) | |
| A61K 39/09 | (2006.01) | |
| A61K 38/16 | (2006.01) | |
| A61K 39/085 | (2006.01) | |

(52) U.S. Cl.
CPC ............. *A61K 39/092* (2013.01); *A61K 38/164* (2013.01); *A61K 39/0008* (2013.01); *A61K 39/085* (2013.01); *A61K 2039/545* (2013.01); *A61K 2039/552* (2013.01); *A61K 2039/58* (2013.01)

(58) Field of Classification Search
CPC .................................................. A61K 39/092
See application file for complete search history.

(56) References Cited

U.S. PATENT DOCUMENTS

2008/0031897 A1*    2/2008    Alderberth et al. ........ 424/237.1

FOREIGN PATENT DOCUMENTS

| CN | 15-09725 A | 7/2004 |
|---|---|---|
| JP | H09-110704 A | 4/1997 |
| WO | WO-91/12818 A1 | 9/1991 |
| WO | WO-01/49319 A1 | 7/2001 |
| WO | WO-03/031471 A1 | 4/2003 |
| WO | WO-2006/009501 A1 | 1/2006 |

OTHER PUBLICATIONS

Lonnqvist, A., et al, "Neonatal exposure to staphylococcal superantigen improves induction of oral tolerance in a mouse model of airway allergy." European Journal of Immunology, 2009, vol. 39, pp. 447-456.
Miron, N., et al., "Staphylococcal enterotoxin A: a candidate for the amplification of physiological immunoregulatory responses in the gut." Microbiology and Immunology, 2010, vol. 54, pp. 769-777.
Collins, L., et al., "Mucosal Tolerance to a Bacterial Superantigen Indicates a Novel Pathway to Prevent Toxic Shock." Infection and Immunity, May 2002, vol. 70, No. 5, pp. 2282-2287.
Akiyama, T., et al., "Possible Role of *Streptococcus pyogenes* in Mucoculaneous Lymph Node Syndrome. XV. Potential Utility of *Streptococcal pyrogenic* Exotoxin Toxoid for the Prophylaxis and Treatment of MCLS." Acta Paediatr Jpn, Oct. 1992, vol. 34, No. 5, pp. 516-524.
International Search Report dated Aug. 27, 2013 in Application No. PCT/SE2013/050094, filed Feb. 5, 2013.
Comans-Bitter et al., Immunophenotyping of blood lymphocytes in childhood Reference values for lymphocyte subpopulations, The Journal of pediatrics, 130(3) (1997): 388-393.
Faldyna et al., Lymphocyte subsets in peripheral blood of dogs—a flow cytometric study, Veterinary immunology and immunopathology, 82(1) (2001): 23-37.
Otani et al., Flow cytometric analysis of canine umbilical cord blood lymphocytes, Journal of Veterinary Medical Science, 70(3) (2008): 285-287.
Kappler et al., Vβ-Specific Stimulation of Human T Cells by Staphylococcal Toxins, *Science* 244(4906) (1989): 811-813.
Choi et al. Interaction of *Staphylococcus* aureus toxin "superantigens" with human T cells. Proceedings of the National Academy of Sciences 86(22) (1989): 8941-8945.
White et al. The Vβ-specific superantigen staphylococcal enterotoxin B: stimulation of mature T cells and clonal deletion in neonatal mice, Cell 56(1) (1989): 27-35.
Callahan et al. Stimulation of B10. BR T cells with superantigenic staphylococcal toxins, The Journal of Immunology 144(7) (1990): 2473-2479.
Kotb et al. An immunogenetic and molecular basis for differences in outcomes of invasive group A streptococcal infections, Nature medicine 8(12) (2002): 1398-1404.
Llewelyn et al. HLA class II polymorphisms determine responses to bacterial superantigens, The Journal of Immunology, 172(3) (2004): 1719-1726.

(Continued)

*Primary Examiner* — Albert Navarro

(74) *Attorney, Agent, or Firm* — Saliwanchik, Lloyd & Eisenschenk

(57) ABSTRACT

The present invention regards use of a bacterial superantigen for administration onto the mucous membrane of a domestic non-human mammal for the prevention of inflammatory disorder, such as allergies, autoimmune and inflammatory diseases.

21 Claims, 5 Drawing Sheets

(56) References Cited

OTHER PUBLICATIONS

Figure 1A:
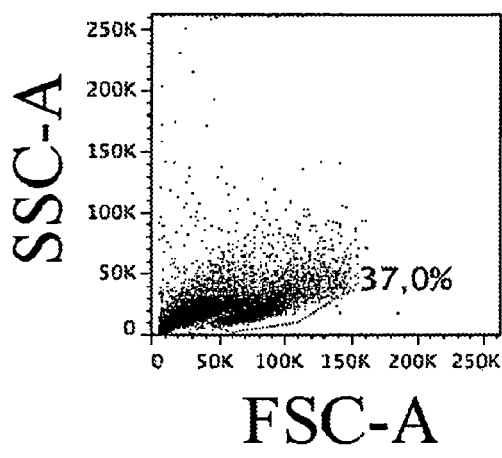

Yuhki et al. Comparative genomic structure of human, dog, and cat MHC: HLA, DLA, and FLA, Journal of Heredity, 98(5) (2007): 390-399.

Holladay et al., Development of the murine and human immune system: differential effects of immunotoxicants depend on time of exposure, Environmental health perspectives, 108(Suppl. 3) (2000): 463.

Day, M. J., Immune system development in the dog and cat, Journal of comparative pathology, 137 (2007): S10-S15.

Fraser, John D., High-affinity binding of staphylococcal enterotoxins A and B to HLA-DR, (1989): 221-223.

Marrack et al., The staphylococcal enterotoxins and their relatives, Science, 248(4956) (1990): 705-711.

* cited by examiner

PREVENTION OF INFLAMMATORY DISORDERS IN DOMESTIC NON-HUMAN MAMMALS

CROSS-REFERENCE TO RELATED APPLICATIONS

This application is the U.S. national stage application of International Patent Application No. PCT/SE2013/050094, filed Feb. 5, 2013, which claims priority to Swedish Application No. 1250090-6, filed Feb. 8, 2012, the disclosures of each of which are incorporated herein by reference in their entirety.

TECHNICAL FIELD

The invention refers to the use of a bacterial superantigen for administration onto the mucous membrane of a domestic non-human mammal for the prevention of inflammatory disorder, such as allergies, autoimmune diseases and inflammatory diseases.

BACKGROUND

A number of diseases are characterized by an exaggerated or untoward immune reactivity against harmless antigens. Such diseases include allergies, autoimmune diseases and inflammatory diseases. Normally, immune responses to harmless antigens are suppressed, a mechanism called tolerance. Tolerance to specific antigens, either exogenous or endogenous, may be induced either by mucosal or systemic exposure. Tolerance occurs because helper T-cells are deleted, paralyzed or suppressed by other T-cells, so called regulatory T-cells.

Allergies

Allergies are defined as enhanced immune reactivity to one or several harmless environmental antigens, so called allergens. In IgE-mediated allergies, the allergic individual mounts an IgE-antibody response to proteins in foodstuffs, pollens, animal dander, etc. The IgE-antibodies are produced by plasma cells developed from B-cells with specificity for a certain allergen. To become an IgE-producing plasma cell, the B-cell must receive help from a T-cell which is specific towards the same allergen. Activation of the T-cell by an allergen leads to the production of cytokines which promotes maturation of the B-cell into a plasma cell that produces IgE. The cytokines IL-4 and IL-13 are especially important in this respect. The subset of T-cells that produce such cytokines and help B-cells to become IgE-producing plasma cells, are called "Th2 cells" (Th=T helper cell). They commonly produce IL-5, a cytokine which promotes maturation of eosinophils in the bone marrow and activation of such eosinophils that arrive to the tissue where an allergic reaction takes place. Once IgE-antibodies are formed, they attach to masT-cells in the tissues, for example around blood vessels and in the respiratory and gastro-intestinal tracts. When the allergic individual is exposed to the allergen, e.g. via inhalation or ingestion, minute amounts of intact protein allergen is taken up into the circulation, reaches the masT-cells and binds to the IgE-antibodies. Hereby the masT-cell becomes activated and secretes a range of mediators that trigger the allergic reaction leading to symptoms forming disease entities such as hay fever, asthma, urticaria, atopic eczema, food allergy and allergic anaphylaxis.

Allergy is much more common in industrialized countries compared to developing countries, which also applies to autoimmune and inflammatory disorders. This has led to the speculation that exposure to microbes affords proper maturation of the developing immune system. However, it is not known which types of microbes are important for this to occur. There is an endless variety of bacteria, viruses and parasites, some of which might be important in providing the right type of stimuli to the immune system, others which may be ineffective, or even increase the risk of developing hypersensitivity or inflammation. For example, the microflora of the gastro-intestinal tract consists of several hundred species, some which are aerobic, while most are obligate anaerobes. The colonizing bacteria can be both Gram-positive and Gram-negative which each differ greatly in cell wall structure and their effects on the immune system.

*Staphylococcus aureus* Enterotoxins—Superantigens

Certain bacteria produce toxins, i.e. protein molecules with highly damaging potential. Most bacteria which produce toxins are pathogenic, i.e. cause disease. But toxin-producing bacteria may also reside in the normal flora of the respiratory and/or gastrointestinal tracts without causing harm. For example, newborn human infants are commonly colonized by toxin-producing *Staphylococcus aureus* (*S. aureus*) in their intestines during their first year of life without showing any symptoms from this colonization. The toxins these strains produce, e.g. *S. aureus* enterotoxin A, B, C or D, or TSST-1 (toxic shock syndrome toxin-1) have so called superantigen function.

Superantigens have a bifunctional binding capacity: they bind both to the major histocompatibility complex II (MHC II) molecule of an antigen-presenting cell and to the T-cell receptor. Whereas a normal antigen only binds to T-cells that have specificity towards just that antigen, the "superantigen" binds to all T-cells that share one certain β-chain in their receptor, i.e. belongs to a certain Vβ-family. This means that they bind to and activate a large proportion (10-30%) of the T-cells in human beings or animals, resulting in a massive cytokine production that may lead to shock and severe symptoms, even death. This is the mechanism behind toxic shock syndrome caused by superabsorbent tampons. TSST-1 producing *S. aureus* may colonize the tampon and produce TSST-1 which is absorbed across the vaginal epithelium and cause shock. A method to prevent the development of superantigen-induced shock may be to expose mucosal surfaces to the particular superantigen prior to challenge, which leads to specific tolerance to that superantigen (but not other antigens). This desensitization has been attributed to production of IL-10 (Collins et al., Infection and Immunity, Vol. 79, No. 5, 2002).

Toxin-producing *S. aureus* have been implicated in the pathogenesis of eczema, because eczematous skin lesions are often colonized by *S. aureus*. It has been suggested that toxins elaborated by *S. aureus* can worsen the reaction by stimulating T-cells, leading to tissue damage.

However, this ability of superantigens to stimulate T-cells has been suggested as a therapeutic treatment of cancers, infectious and allergic diseases by the employment of the superantigen to activate specific immune responses (US 2001/046501), and in WO 2003/002143 engineered superantigens including staphylococcal enterotoxins and TSST-1 are used in treatment of various forms of cancer. In WO 1991/12818 to Lamb et al. superantigens are parenterally administered to reduce the immune response including T-cells in order to prevent or treat rejection reactions, autoimmune disease, allergic disease and harmful responses to infectious agents. The mechanism proposed is via deletion of T-cells or via induced anergy of T-cells. However a treatment that results in anergy or deletion of T-cells would not be recommended as prevention for allergy in children since decreased T-cell function would lead to a poor defense against infections.

Regulatory T-Cells (Tregs)

It is believed that allergy, autoimmune and inflammatory disorders are prevented by so called regulatory T-cells (Treg). These cells suppress activation of helper T-cells and thereby down-regulate many types of immune responses. One population of regulatory T-cells, named CD25+Treg (or CD4+ CD25+CTLA-4+ T-cells), are CD4-positive T-cells that have a high density of CD25 on their cytoplasm which functions in intracellular expression. CD25+ Tregs have a capacity to down-regulate the expansion and activation of helper T-cells. Helper T-cells are T-cells which enhance immune responses such as T-cell mediated cytotoxicity, delayed type hypersensitivity and antibody production. Another marker that can be used to identify Tregs is messenger RNA for the gene Foxp3.

Tregs are produced in the thymus and exit to the periphery in the first days of life in mice. In humans, cells of the Treg phenotype are present at birth, but express lower levels of Foxp3 compared with cells from adults. It has been described that the number and function of CD25+ Treg can be increased by in vitro stimulation with polyclonal activators as well as specific antigens and transfer of these antigen-expanded cells into mice results in delayed development of autoimmune disease in susceptible mice. Repeated injection of the superantigen *Staphylococcus aureus* enterotoxin A (SEA) into Vβ3– and Vβ8 transgenic mice resulted in potentiated suppressive function of CD25+ Treg as well as induction of suppressive function in CD25– T-cells (T-cells that do not express CD25 on their surface and which cannot suppress helper T-cell functions). Superantigen administrated in such a way also results in an activation followed by a severe reduction in the number of T-cells in the animal (Grundstrom et al. Jour. of Immunology, 2003, 170, 5008-5017). This observed activation/reduction together with the fact that superantigen in the blood circulation leads to shock are the main reasons why Staphyloccocal enterotoxins administered into the blood is an unsuitable method of treatment.

Regulatory T-cells, so called Treg, have come into focus recently. As discussed above, Tregs have the ability to down-regulate many types of untoward immune responses, including allergy, autoimmunity and inflammatory bowel disease. Many methods have been designed to expand and activate this cell type in vitro with the purpose to transfer these expanded and activated cells back to the individual from whom they were derived.

It is previously known that activation of the human immune system by mucosal exposure to *S. aureus* toxins having a superantigen function, in order to expand and activate regulatory Tcells in vivo in early infancy, may be used to prevent inflammatory disorders, such as allergy. Document EP 1 789 083 B1 discloses use of a bacterial superantigen for prevention of an inflammatory disorder in newborn infants. Further, Lönnqvist et al (cf. European Journal of Immunology, 2009, vol. 39, 447-456) has shown that neonatal exposure to staphylococcal superantigen improves induction of oral tolerance in a mouse model of airway allergy.

Treatment of allergy and other inflammatory disorders in humans in general is a well studied field. However, many domestic mammals, such as dogs, cats and horses, also suffer from inflammatory disorders, such as allergy. In general, the options for alleviating inflammatory disorders in non-human mammals are very limited, due to lack of understanding of the non-human immune system.

The rising trend of allergy development is evident not only among humans but also among pet dogs. A growing number of pet dogs suffer from diseases due to lack of immunological regulation. Today allergy is one of the most common health problems for dogs, and one of the leading causes of visits to the veterinary office. It is estimated that 10-15 percent of all dogs, irrespective of breed, develop allergy. According to Agria Pet Insurance, one of the world's leading animal insurers, diagnoses having to do with allergies have increased by as much as 90 percent over the last decade and approximately 20 percent of all veterinary visits are related to allergies.

Many of the factors linked to increasing incidence of allergic disorders in humans are also consistent with the changing environment of dogs, such as decreased early infections, changes in diet, an urban environment, and other factors that decrease circulation of microbes and, hence, deprive the immune system of key stimulatory signals in early life Two of the most common allergic disorders in pet dogs are canine atopic dermatitis (CAD) and food allergies. Canine atopic dermatitis is a pruritic skin disease with typical location and appearance, i.e. affecting the face, ears, paws, extremities, and/or ventrum. Often, the dog also has IgE antibodies to environmental allergens, but this is not clearly linked to disease presentation, also known as sensibilization. Otitis externa and skin infections due to staphylococci and yeasts commonly accompany CAD, due to impaired skin barrier defense in this disease. The typical age of onset of CAD is reported to be between 6 months and 3 years.

CAD shares many features with human atopic dermatitis, such as similar histopathology, pruritus as the predominant clinical sign and impaired skin barrier function. Just as for human allergies, no prophylactic or curative treatment is at hand for these disorders. Canine allergy is a complex, lifelong disease generally requiring lifelong treatment.

Allergen avoidance and anti-allergic drugs are the two treatment options. Since environmental antigens often cannot be avoided, the strategy of allergen avoidance is seldom effective. Symptoms may be relieved by antihistamines; local inflammation is curbed by topical steroids and, in more severe cases, T-cell activation can be dampened by cyclosporine. For many dogs with CAD, the response to pharmacotherapy is unsatisfactory. In these cases, allergen-specific immunotherapy, also known as hyposensitization, can be used. This is a practice designed for human allergic patients, administering gradually increasing quantities of and allergen extract to an allergic patient to ameliorate the symptoms associated with subsequent exposure to the allergen. At this time, there are few guidelines on when and how to use immunotherapy in dogs with CAD.

There is thus a need for improved methods to prevent inflammatory disorders, such as allergies, in domestic non-human mammals and particularly in dogs, cats, and horses.

SUMMARY OF INVENTION

The present invention discloses a pharmaceutical composition comprising a bacterial superantigen for use in prevention, or prophylactic treatment, of an inflammatory disorder in domestic non-human mammals by mucous membrane administration in newborn domestic non-human mammals as defined below. Examples of superantigens include, but are not limited to, the *Staphylococcus aureus* enterotoxins A, B, C1, C2, C3, D, E, G or H, enterotoxin-like toxins Q, M or K, and TSST-1, or derivatives thereof. The inflammatory disorder may be allergy, such as food allergy or atopic dermatitis, an inflammatory disease, or an autoimmune disease.

In one aspect of the invention, the pharmaceutical composition comprising the superantigen, is administered to a newborn non-human mammal no later than 3 months after birth, preferably no later than 2 weeks after birth, more preferably no later than 10 days after birth, even more preferably no later than 7 days after birth.

In one aspect of the invention, the pharmaceutical composition comprising the superantigen is administered onto the nasal mucous membrane or onto mucous membrane in the oral cavity. Further, the pharmaceutical composition comprising the superantigen may be administered onto the intestinal mucous membrane.

In an additional aspect of the invention, the use of the pharmaceutical composition comprising the bacterial superantigen provides a method for preventing, e.g. reduce the incidence of, allergy development, autoimmune and inflammatory disorders non-human mammals.

The domestic non-human mammal may be a dog, a cat, or a horse. In an aspect of the invention, the domestic animal is dog or cat.

Further advantageous features of the invention are defined in the dependent claims. In addition, advantageous features of the invention are elaborated in embodiments disclosed herein.

The present invention has the advantage that inflammatory disorders, such as allergies, may be prevented in domestic non-human mammals and particularly in animals, such as dogs. Even though the preventive effect is known from humans, it is surprising that the same effect is obtained in non-human mammals, since the immune system differs between humans and non-humans.

DETAILED DESCRIPTION

By the term "Inflammatory disorders or reactions" herein and in the accompanying claims is meant diseases and disorders caused by immune hyper-reactivity to endogenous or exogenous antigens comprising diseases such as allergies; e.g. food allergy, hay fever, asthma, urticaria, eczema, and anaphylactic reactions; inflammatory diseases; e.g. ulcerative colitis, and Mb Crohn; and autoimmune diseases; e.g. type 1 diabetes, autoimmune gastritis, autoimmune thyreoiditis, autoimmune haemolytic anemia thrombocytopenia, and multiple sclerosis.

As described above, *S. aureus* and its superantigen production has been regarded as detrimental in development of allergy. It has been shown that exposure to staphylococcal superantigen in vivo via colonization of the mucosal surfaces in the gastro-intestinal and/or respiratory tracts affords protection from atopy and eczema, which is surprising, since the general opinion is that it is harmful to be colonized by *S. aureus* and that their toxins could drive the immune system into an allergic response by their superantigen function.

Exposure to *S. aureus* toxins with superantigen function via injection into the blood circulation carries an unacceptable risk of side-effects. In contrast, there may be no increased occurrence of gastro-intestinal or other side-effects in domestic non-human mammals colonized in their intestines with toxin-producing *S. aureus* compared to domestic non-colonized non-human mammals.

The present invention discloses that toxin producing *S. aureus* by their strong T-cell-activating effects are able to induce expansion and/or maturation of regulatory T-cells that may later afford protection from allergy and also other diseases caused by untoward immune activation, not only in human, but also in domestic mammals. Given the differences between the immune systems of newborn human on one hand and newborn domestic mammals, such as dogs, on the other, this finding is far from expected.

B-cells constitute a large proportion of lymphocytes in newborn dogs, i.e. around 40%, while they only make up 12% of the lymphocytes in human neonates (cf. Comans-Bitter W M et al. "*Immunophenotyping of blood lymphocytes in childhood. Reference values for lymphocyte subpopulations*" in J. Pediatr. 130:389-93, 1997, and Faldyna M. Et al. "*Lymphocyte subsets in peripheral blood of dogs—a flow cytometric study*." in Vet. Immunol. Immunopathol. 82:23-37, 2001, respectively). Regarding T-cells, they represent 60-70% of the lymphocytes in human neonates, as compared to only about 50% in dogs (cf. Ottani I et al. "*Flow Cytometric Analysis of canine umbilical cord blood lymphocytes*." in J. Vet. Med. Sci. 70:285-7, 2008, and Faldyna M. Et al. "*Lymphocyte subsets in peripheral blood of dogs—aglow cytometric study*." in Vet. Immunol. Immunopathol. 82:23-37, 2001, respectively).

More importantly, there is also a striking difference in T-lymphocyte subsets between dogs and humans, and in how these subsets change with age over time. In newborn infants, CD4+ lymphocytes increase substantially during the first weeks of life; both in absolute numbers and in relative proportion (cf. Comans-Bitter W M et al. "*Immunophenotyping of blood lymphocytes in childhood. Reference values for lymphocyte subpopulations*" in J. Pediatr. 130:389-93, 1997). The ratio of CD4+/CD8+ T-cells is around 2 in neonates and increases during the first weeks. This, increase in CD4+ T lymphocytes likely occurs in response to microbial stimulation.

However, a completely different pattern is observed in dogs. Dogs show a progressive decrease in CD4+ T-lymphocytes from birth and onwards, both in absolute counts and in relative numbers (Faldyna M. Et al. "*Lymphocyte subsets in peripheral blood of dogs—a flow cytometric study*." in Vet. Immunol. Immunopathol. 82:23-37, 2001). The ratio of CD4+/CD8+ T-cells is 7.6 in cord blood, 7 in puppies around birth, and thereafter decrease continuously to around 2 in adult dogs (cf. Ottani I et al. "*Flow Cytometric Analysis of canine umbilical cord blood lymphocytes*." in J. Vet. Med. Sci. 70:285-7, 2008, and Faldyna M. Et al. "*Lymphocyte subsets in peripheral blood of dogs—a flow cytometric study*." in Vet. Immunol. Immunopathol. 82:23-37, 2001, respectively). In dogs, the number of CD8+ T-lymphocytes increases continuously after birth.

These differences indicate that there is a fundamental difference in how humans and dogs respond to microbial stimulation after birth. Whereas humans respond with preferentially an increase in CD4+ T-cells, dogs seem to respond with an expansion of CD8+ T-cells. It is, thus, surprising that an increase in CD25+FOXP3+ CD4+ T-cells in the dog exposed to the high dose of *S. aureus* superantigen SEC2 was observed (cf. Example 2 herein below). This cell population likely represents newly activated CD4+ T-cells, and, thus, stimulation with the microbial product SEC2 resulted in stimulation and activation of CD4+ T-cells in this dog. Further, in vitro findings (cf. cf. Example 1 herein below) also Tregs can be induced stimulation with other superantigens, including *Staphylococcus aureus* enterotoxin A, B, C1, C2, and C3 as well as toxic shock syndrome toxin-1 (TSST-1)

Thus, it was surprising to find that the concept disclosed in EP 1 789 083 B1 also may be applied in domestic animals, i.e. activation of the immune system by *S. aureus* toxins with superantigen function can be exploited to afford the natural immune activation of the immune system of a domestic non-human mammal. Superantigens are a class of toxins whose amino acids sequence is relatively conserved among the different subgroups. Further, the three dimensional structure, being more important than sequence homology as it affects the binding properties of the toxin, is very similar among different superantigens resulting in similar functional effects among different groups. Thus, also other superantigens than staphylococcal may be used.

An embodiment of the invention relates to a pharmaceutical composition comprising a bacterial superantigen for use in prevention, or prophylactic treatment, of an inflammatory disorder in a domestic non-human mammal. Typical examples of domestic non-human mammal are dogs, cats, and horses. A preferred example of a domestic non-human mammal is a dog. While such a pharmaceutical composition may be used to prevent, or prophylactically treat, an inflammatory disorder in any dog, as dogs in general may develop allergies, allergic reactions are especially common in terriers, setters, retrievers, and flat-faced breeds. High-risk breeds include West Highland White Terrier, Boston Terrier, Boxer, Staffordshire Bullterrier and French Bulldog. Thus, those breeds, including the high-risk breeds, are of special interest to administer the present pharmaceutical composition to in order to prevent, or prophylactically treat, an inflammatory disorder. In prevention, or prophylactic treatment, of an inflammatory disorder the pharmaceutical composition is administrated onto mucous membranes of the domestic mammal.

Due to the risk of side effects, administration by injection, e.g. intravenous, intramuscular or subcutaneous injections is from a safety perspective not an open route for administrating the pharmaceutical composition. On the contrary administration onto mucous membrane has been found to provide the desired prophylactic effect with low risk of side effects. In administration onto mucous membrane, the pharmaceutical composition may be administered onto the nasal mucous membrane, i.e. nasally, onto mucous membrane in the oral cavity, e.g. sublingually or buccal, or onto the intestinal mucous membrane, i.e. orally. In order to exert a prophylactic effect, the pharmaceutical composition should be administered early in life, i.e. to newborn domestic non-human mammals. Preferably, the pharmaceutical composition is thus administered within 3 months after birth.

According to an embodiment, the pharmaceutical composition is administered within much less than 3 months after birth, particularly within two weeks after birth, more particularly within 10 days after birth, even more particularly within 7 days after birth. Early administration of the composition has been found to be necessary for activation of immunological tolerance mechanisms. This is believed to be due to the fact that the canine immune system seems to be more susceptible to induction of tolerance early in life.

The pharmaceutical composition may be administered in a single dose or in multiple doses. According to an embodiment the pharmaceutical composition is administered multiply, i.e. at least two times, such as at least three times, at distinct occasions. Upon multiple administration, the dosage regimen may be administration on consecutive days (e.g. day 0 and day +1 or day 0, day +1 and day +2, respectively), administration every second day (e.g. day 0 and day +2, or day 0, day +2 and day +4, respectively), or administration every third day (e.g. day 0 and day +3, or day 0, day +3 and day +6, respectively). Further, also longer intervals, such as 1 or 2 weeks, may be used for multiple administrations.

When used herein, "prevent/preventing" should not be construed to mean that a condition and/or a disease never might occur again after use of the pharmaceutical composition to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use. Thus, prevent may be interpreted as reducing the coincidence of a given condition. Further, the term may be interpreted as prophylactic treatment.

Human infants are commonly colonized by *Staphylococcus aureus* (*S. aureus*) in their intestines. *S. aureus* are known to produce toxins denoted superantigens (SAg), which are proteins with pronounced T-cell activating properties. More than 20 distinct SAgs have been characterized from different *S. aureus* strains, including, e.g. *S. aureus* enterotoxins (SE) A, B, C1, C2, C3, D, E, G and H, *S. aureus* enterotoxin-like toxin (SE-I)-Q, -M and -K, as well as toxic shock syndrome toxin (TSST)-1. Most isolates of *S. aureus* produce several SAgs.

Pharmaceutical composition may be provided with bacterial superantigens in at least two manners. Firstly, isolated, purified superantigen(s) may be added to a carrier. Secondly, a pharmaceutical composition may be provided with a bacterial strain producing superantigen(s). Examples of preferred strains are of *Staphylococcus aureus* and streptococcal strains producing superantigen(s), such as *Streptococcus pyogenes*.

Upon use of isolated, purified superantigen(s) the exact dose of the superantigen is easier to control. Further the risk for an infection is eliminated as no viable material is administered. On the other hand, use of bacterial strain producing superantigen(s) most likely provides a more efficient way of inducing tolerance as a cocktail of superantigens as well as other structures will be produced by the bacteria and presented to the subjected to whom the pharmaceutical composition is administered. However, use of bacterial strains, producing superantigen(s), implies a risk for infections and less control of the dose regimen.

According to an embodiment, the pharmaceutical composition comprises at least one *Staphylococcus aureus* strain producing superantigen(s).

According to an embodiment, the pharmaceutical composition comprises at least one *Staphylococcus aureus* superantigen, such as at least one *S. aureus* enterotoxin, at least one *S. aureus* enterotoxin-like toxin, and/or toxic shock syndrome toxin (TSST)-1. According to an embodiment, the pharmaceutical composition comprises at least one of the *Staphylococcus aureus* enterotoxins A, B, C1, C2, C3, D, E, G or H, at least one of the *Staphylococcus aureus* enterotoxin-like toxins Q, M or K, and/or toxic shock syndrome toxin (TSST)-1.

*Staphylococcus aureus* enterotoxins A and B (SEA and SEB) are generally known for their high level of toxicity, which is well-described in literature. In the herein disclosed in-vitro canine PBMC studies (cf. Example 1), *Staphylococcus aureus* enterotoxins C2 (SEC2) was found to be less potent compared to SEA and SEB, while still showing adequate immune activation. The herein disclosed in-vivo trials (cf. Example 2) have confirmed immunological activation by SEC2 without any adverse effects. Use of a less toxic superantigen, still providing adequate immune activation and thereby induction of tolerance, is preferred to avoid side-reactions. Thus, the pharmaceutical composition according to an embodiment comprises SEC2.

As already described, SAgs are a class of toxins whose amino acids sequence is relatively conserved among the different subgroups. Further, the three dimensional structure, affecting the binding properties of the toxin, is very similar among different SAgs resulting in similar functional effects among different superantigens. As an example, Staphylococcal SAgs share sequence homology and mode of action with streptococcal SAgs, termed streptococcal pyrogenic exotoxins (Spe), including streptococcal pyrogenic exotoxin A, C, G, H, or I, streptococcal mitogenic exotoxins (SME)-Z 1 and 2, and streptococcal superantigen A (SSA). As seen in FIG. 4, the streptococcal SAgs SpeH and SpeA belong to group II which also contains the staphylococcal SAgs SEB and SEC.

Furthermore, streptococcal superantigen SpeI is a member of Group V, which also contains the staphylococcal superantigen SEI-Q, SEI-M and SEI-K.

Both staphylococcal and streptococcal SAgs act by binding to and activating a large proportion of all T-cells by binding to a conserved part of the T-cell receptor. Whereas a normal antigen only binds to T-cells that have specificity towards just that antigen, the "superantigen" binds to all T-cells that share one certain β-chain in their receptor, i.e. belongs to a certain Vβ-family. This means that they bind to and activate a large proportion (10-30%) of the T-cells in human beings or animals, resulting in a massive cytokine production.

Figure 4:
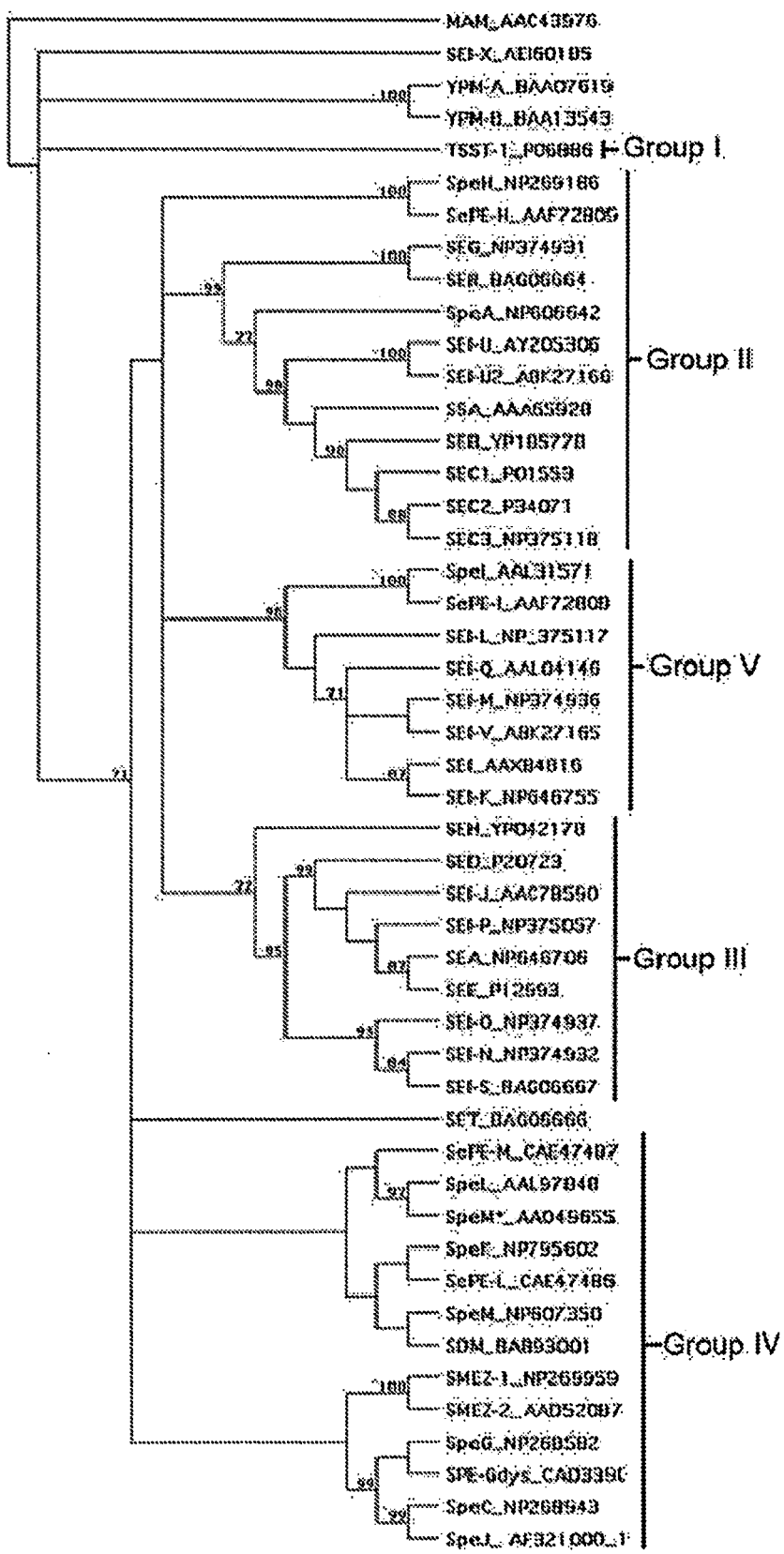

Due to these similarities not only staphylococcal, but also streptococcal SAgs may be used for prevention of inflammatory disorders in domestic non-human mammals. According to an embodiment, the pharmaceutical composition does thus comprise at least one streptococcal superantigen, such as Streptococcal pyrogenic exotoxin A (SpeA) or Streptococcal pyrogenic exotoxin H (SpeH). SpeA and SpeH share sequence homology and mode of action with SEC2 and belongs to the same phylogenetic group (cf. group II in FIG. 4).

As already described, the pharmaceutical composition may also be provided with a bacterial superantigen by adding a superantigen producing bacterial strain. According to an embodiment, the pharmaceutical composition does thus comprise at least one streptococcal strain producing superantigen.

Not only natural superantigens may be used to prevent inflammatory disorders in domestic non-human mammals, but also derivative thereof as long as they have superantigen activity. As superantigens are proteins, various ways of obtaining derivatives are known to the skilled person, such as amino acid substitution, deletion, or insertion as well as addition at the N-terminus or C-terminus of the protein. Substitution, insertion and addition may be performed with natural as well as non-natural amino acids. One type of derivatives of interest may be fragments of natural superantigen, i.e. proteins and peptides consisting of only part of the sequence of the full-length protein. Further, natural superantigens may be substituted with HIS-tags to facilitate purification, as well as PEG-moieties and other types of moieties affecting the solubility of the protein.

Inflammatory Disorder

Inflammatory disorders are disorders caused by immune hyper-reactivity to endogenous as well as exogenous antigens. They include allergies, autoimmune diseases and inflammatory diseases.

Examples of allergies include food allergy, hay fever, asthma, urticaria, eczema, anaphylactic reactions, and atopic dermatitis, e.g. canine atopic dermatitis.

Examples of inflammatory diseases include ulcerative colitis and Mb Crohn.

Examples of autoimmune diseases include type 1 diabetes, autoimmune gastritis, autoimmune thyreoiditis, autoimmune haemolytic anemia, thrombocytopenia, and multiple sclerosis.

According to an embodiment, the inflammatory disorder to be prevented by use of a pharmaceutical composition comprising a bacterial superantigen is food allergy or atopic dermatitis, e.g. canine atopic dermatitis.

Pharmaceutical Compositions

The strains, toxins and the superantigen(-s) disclosed herein may be isolated in any level of purity by standard methods and purification can be achieved by conventional means known to those skilled in the art, such as distillation, recrystallization and chromatography.

The strains, toxins and the superantigen(-s) disclosed herein are administered as a pharmaceutical composition, i.e. in combination with pharmaceutically acceptable carrier and/or diluent. The administration may be carried out in single or multiple doses.

Pharmaceutical compositions may, for example, be in the form of tablets, pills sachets, vials, hard or soft capsules, aqueous or oily suspensions, aqueous or oily solutions, emulsions, powders, granules, syrups, elixirs, lozenges, reconstitutable powders, liquid preparations, sprays, creams, salves, jellies, gels, pastes, ointments, liquid aerosols, dry powder formulations, or HFA aerosols.

The pharmaceutical compositions may be in a form suitable for administration through oral, buccal routes, or for administration by inhalation or insufflation (e.g. nasal, tracheal, bronchial) routes.

Depending upon the disorder and patient to be treated and the route of administration, the compositions may be administered at varying doses. A suggested dose concentration of administration of a solution or a suspension of bacterial superantigen(s) is 40 μg/ml. The dose of the superantigen(s) is according to an embodiment in the range 1 to 750 μg per kg bodyweight, such as 15 to 300 μg per kg bodyweight or 30 to 180 μg per kg bodyweight.

Oral, Buccal or Sublingual

For oral, buccal or sublingual administration, the bacterial superantigen may be combined with various excipients. Solid pharmaceutical composition for oral administration often include binding agents (for example syrups and sugars, acacia, gelatin, sorbitol, tragacanth, polyvinylpyrrolidone, sodium lauryl sulphate, pregelatinized maize starch, hydroxypropyl methylcellulose, lactose, starches, modified starches, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone and sodium alginate), disintegrants (such as starch and preferably corn, potato or tapioca starch, alginic acid and certain complex silicates, polyvinylpyrrolidone, sucrose, gelatin, acacia, sodium starch glycollate, microcrystalline cellulose, crosscarmellose sodium, crospovidone, hydroxypropyl methylcellulose and hydroxypropyl cellulose), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols and sodium stearyl fumarate) and fillers (including high molecular weight polyethylene glycols, lactose, sugar, calcium phosphate, sorbitol, glycine magnesium stearate, starch, glucose, lactose, sucrose, rice flour, chalk, gelatin, microcrystalline cellulose, calcium sulphate, xylitol and lactitol). Such compositions may also include preservative agents and anti-oxidants.

Liquid pharmaceutical compositions for oral administration may be in the form of, for example, emulsions, syrups, or elixirs, or may be presented as a dry product for reconstitution with water or other suitable vehicle before use. Such liquid compositions may contain conventional additives such as suspending agents (e.g. sorbitol, syrup, methyl cellulose, hydrogenated edible fats, gelatin, hydroxyalkylcelluloses, carboxymethylcellulose, aluminium stearate gel, hydrogenated edible fats) emulsifying agents (e.g. lecithin, sorbitan monooleate, or acacia), aqueous or non-aqueous vehicles (including edible oils, e.g. almond oil, fractionated coconut oil) oily esters (for example esters of glycerine, propylene glycol, polyethylene glycol or ethyl alcohol), glycerine, water or normal saline; preservatives (e.g. methyl or propyl p-hydroxybenzoate or sorbic acid) and conventional flavoring, preservative, sweetening or colouring agents. Diluents such as water, ethanol, propylene glycol, glycerin and for nations thereof may also be included.

Other suitable fillers, binders, disintegrants, lubricants and additional excipients are well known to a person skilled in the art.

Oral delivery of therapeutic agents in general is a preferred mode of administration due to its convenience and simplicity, both contributing to better patient compliance. Recombinant technology has made available a wider selection of proteins and polypeptides for use as therapeutic agents, and oral delivery of proteins and polypeptides is of increasing interest and value. However, because proteins and polypeptides can be unstable during storage, leading to loss of biological activity, an oral formulation is preferably designed to optimize stability for retention of activity during storage and upon administration. According to an embodiment, the pharmaceutical composition comprising a bacterial superantigen is administered orally.

Formulation factors that require consideration of design of an oral formulation of a protein or polypeptide include the solution behavior of the protein or polypeptide in aqueous and non-aqueous solvents and the effect of ionic strength, solution pH, and solvent type on the stability and structure of the protein or polypeptide. The effect of temperature during formulation on the stability and structure of the protein or polypeptide must also be considered, as should the overall suitability of the formulation for incorporation into an oral dosage form, and particularly into an oral liquid dosage form, such as a gelatin capsule or syrup.

Nasal Administration

For nasal administration or administration by inhalation, a bacterial superantigen may be delivered in the form of a solution, dry powder or suspension. Administration may take place via a pump spray container that is squeezed or pumped by the administrator or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The bacterial superantigen may also be administered via a dry powder inhaler, either as a finely divided powder in combination with a carrier substance (e.g. a saccharide) or as microspheres.

The inhaler, pump spray or aerosol spray may be single or multi dose. The dosage may be controlled through a valve which delivers a measured amount of active compound.

In an embodiment, the pharmaceutical composition comprising the bacterial superantigen may be used in a method for preventing allergy development, autoimmune and inflammatory disorders in non-human mammals, such as domestic animals. The method comprises a step of administering the pharmaceutical composition to the mucous membrane administration of newborn domestic non-human mammals.

The specification of the pharmaceutical composition, the mucous membrane, the route of administration, and the domestic mammal may be as previously described.

In an embodiment, use of a bacterial superantigen for the manufacture of a pharmaceutical composition for mucous membrane administration in newborn domestic non-human mammals for the prevention of an inflammatory disorder is provided.

The specification of the pharmaceutical composition, the mucous membrane, the route of administration, and the domestic mammal may be as previously described.

Without further elaboration, it is believed that one skilled in the art can, using the preceding description, utilize the present invention to its fullest extent. The preferred specific embodiments described herein are, therefore, to be construed as merely illustrative and not limitative of the remainder of the description in any way whatsoever. Further, although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do neither preclude a plurality.

BRIEF DESCRIPTION OF DRAWINGS

The following drawings form part of the present specification and are included to further demonstrate certain aspect of the present invention. The invention may be better understood by reference to one or more of these drawings in combination with the detailed description of the invention.

FIG. 1 shows a gating strategy for FACS analyzed canine PBMC six days after in vitro stimulation with superantigen.

FIG. 2A is a graph showing proliferation and FIG. 2B is a graph showing FoxP3 Treg induction in superantigen stimulated canine PBMC.

FIG. 3A is a graph showing the proportion of CD4-positive T-cells being FoxP3+ over time after stimulation with SEC2 (Loke and Lexi) or placebo (Lovis and Loppan)

3B is a graph showing is a graph showing the proportion of CD4-positive T-cells being Foxp3+CD25+ over time after stimulation with SEC2 (Loke and Lexi) or placebo (Lovis and Loppan)

FIG. 4 is showing the phylogenetics for various superantigens

EXAMPLES

The following examples are included to demonstrate the preferred embodiments of the invention. It should be appreciated by those skilled in the art that the techniques disclosed in the examples which follow are given for the purpose of illustration only and are not intended to limit the scope of the invention.

Example 1

FoxP3$^+$ Regulatory T-Cell Induction in Canine Peripheral Blood Mononuclear Cells (PBMC) Promoted by Superantigen Stimulation PBMC was collected from healthy dogs (Border terrier), by centrifugation on a Percoll gradient. The cells were stained with CellTraceViolett, according to manufactur's instructions (Stemcell technology), in order to measure cell-proliferation. Stained cells (100,000/well) were stimulated with different superantigens, i.e. *Staphylococcus aureus* enterotoxin (SE) A, B, C1, C2, C3 and toxic shock syndrome toxin-1 (TSST-1), at doses ranging from 1 μg/well to 1 pg/well in 37° C. in 5% $CO_2$. Cells were harvested after six days and analyzed for proliferation and expression of CD4 and FoxP3 by flow cytometry. All cells were acquired using FACSCantoII (BD Biosciences) and analyzed with FlowJo software (Treestar inc., Ashland, Oreg.), well known to a person skilled in the art.

Figure 1B:
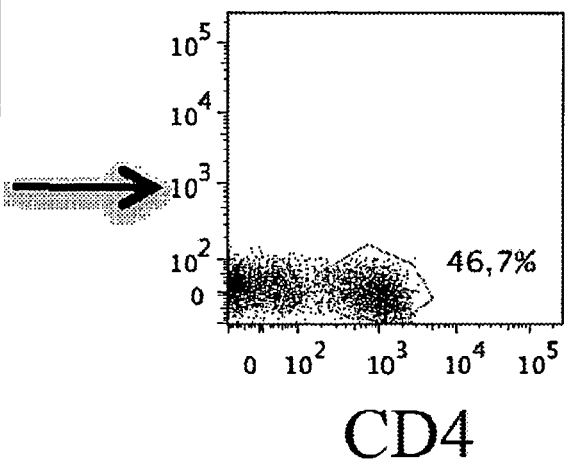
Figure 1C:
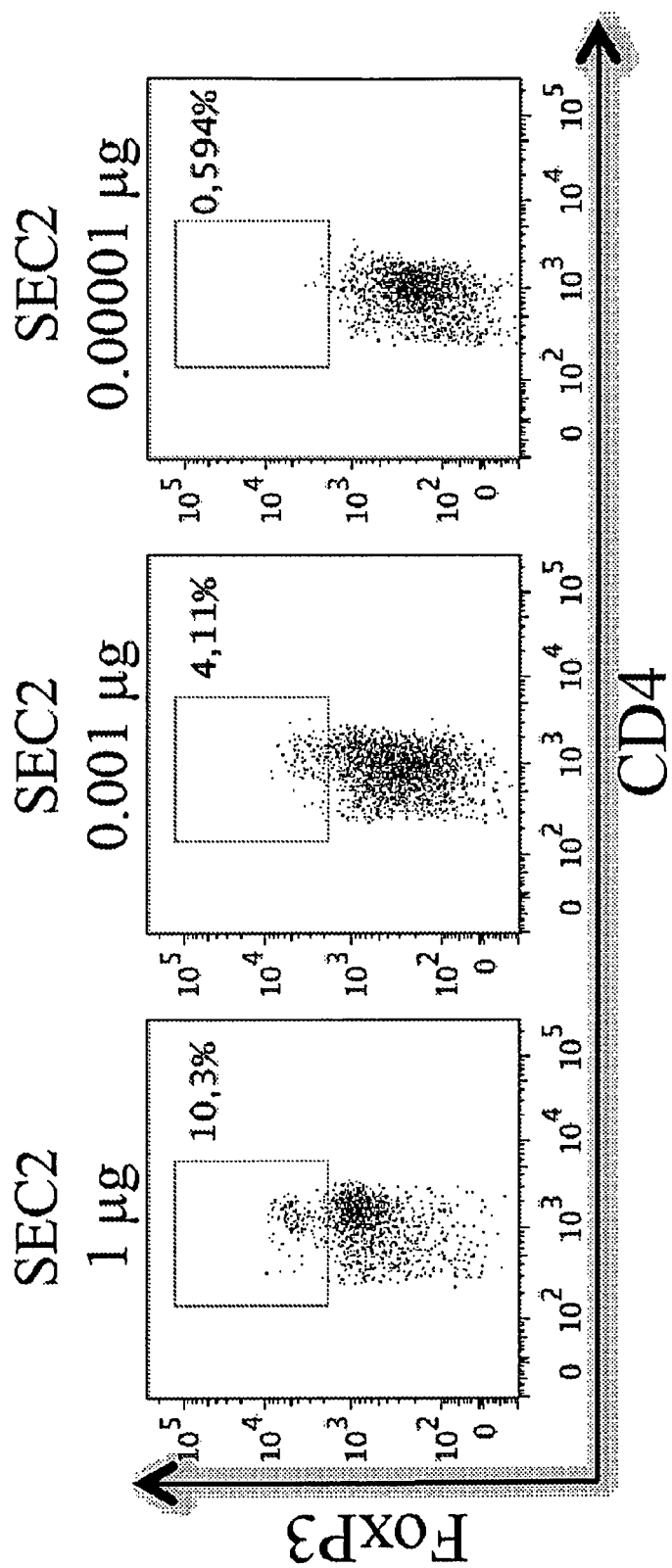
Figure 2A:
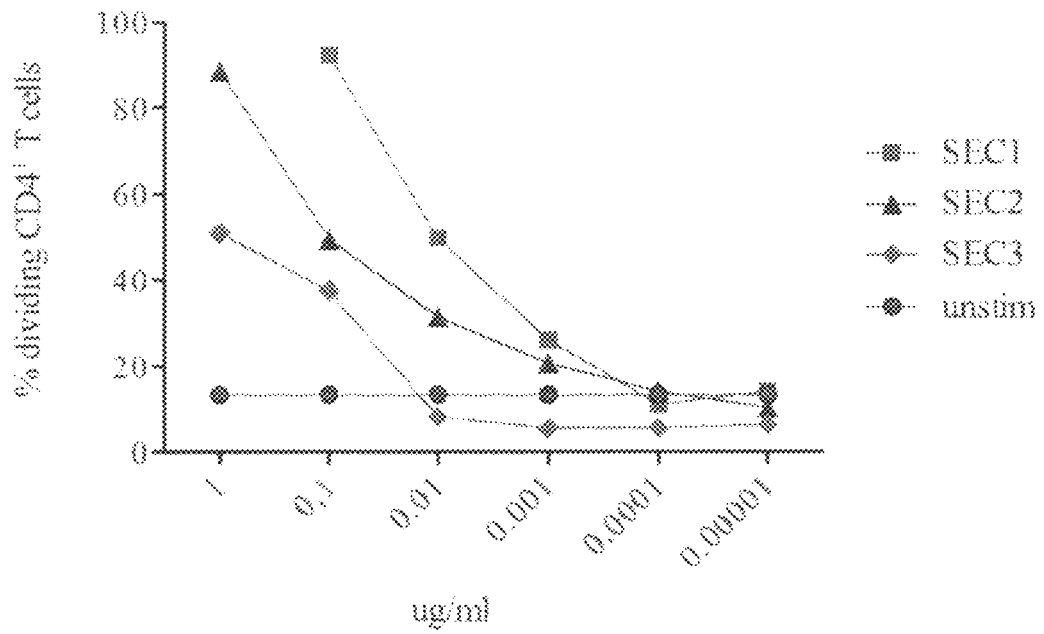
Figure 2B:
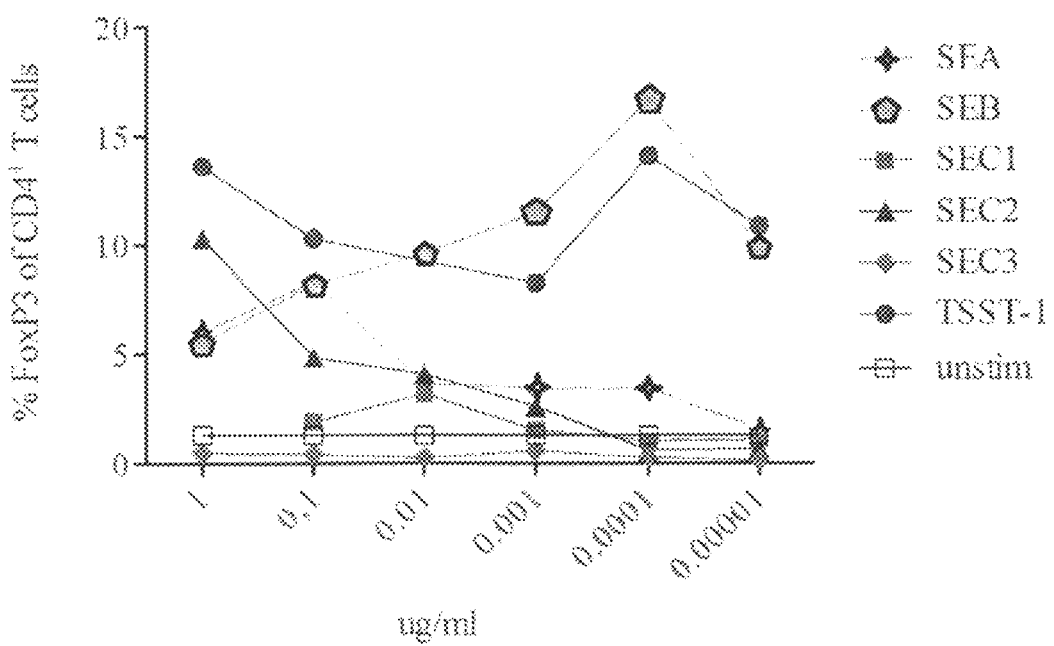

With reference to FIG. 1, the cells were first gated on lymphocytes (FIG. 1A) and from the lymphocytegate CD4+ T-cells were selected and used for the further analysis (FIGS. 1B-C). The CD4+ T-cell stimulatory effect, as measured by proliferation mediated by the different superantigens, was variable. SEA, SEB and TSST-1 were the most potent stimulators whereas SECs were less potent, especially SEC3, as seen in FIG. 2A. When analyzing the presence of regulatory T-cells (Tregs), expressing FoxP3, it was possible to see that the proportion of Tregs among the CD4+ T-cells corresponded to the degree of proliferation (FIG. 2B). These results show that Tregs can be induced from canine PBMC by stimulation with superantigen.

Thus, exposure with superantigens is expected to prevent induction of inflammatory disorders and immune hyperreactivity in a domestic non-human mammal, such as dog.

Example 2

Methodology
Treatment of Newborn Puppies

One litter of 4 Beagle puppies, born at the animal facilities at the Swedish University of Agricultural Sciences, Uppsala, Sweden, was included in the study. One week after birth puppies were given *Staphylococcus aureus* enterotoxin C2 (Toxin Technology, Sarasota, Fla., US) or Placebo (PBS) by oral administration of a 0.5 ml dose. Two puppies received SEC2, one was given a low dose (0.5 μg) and the other a 10-times higher dose (5 μg), and the remaining two were given placebo. The treatments were repeated two times every other day, i.e. each puppy was given three doses in total (day 7, 9 and 11 after birth, respectively). The puppies were monitored continuously during the treatment (vomiting, diarrhea, rectal temperature) and no adverse symptoms were noted.

Flow Cytometric Analysis

Blood samples were collected from the puppies at time point 0, just before the first dose of SEC2 or placebo, and 1, 2, 3 and 4 weeks after the initial dose, respectively. Blood was drawn into heparinised tubes and analysed by flow cytometry within 48 h of collection. For the identification of CD4$^+$CD25$^+$FoxP3$^+$ T-cells and CD4$^+$ FoxP3$^+$CD45RA$^+$ T-cells, staining for cell surface CD4, CD25, CD45RA and intracellular FoxP3 was performed according to standard procedure (eBioscience protocols). The following anti-dog antibodies were used: F488-conjugated anti-CD4 (YKI 302.9), PE-conjugated anti-CD25 (P4A10), and AF647-conjugated anti-FoxP3 (FJK-16s), all from eBioscience, and anti-CD45RA (CA4.1D3) followed by a-mRPE, both from AbD Serotec. Flow cytometry was performed in a FACSCanto (Becton-Dickinson) and the data were analysed with the FlowJo (Tree-Star, Ashland, Oreg.) software.

FoxP3 is a marker for regulatory T-cells, and for recently strongly activated helper T-cells. CD25 is also a marker for both activated T-cells and regulatory T-cells.

Figure 3A:
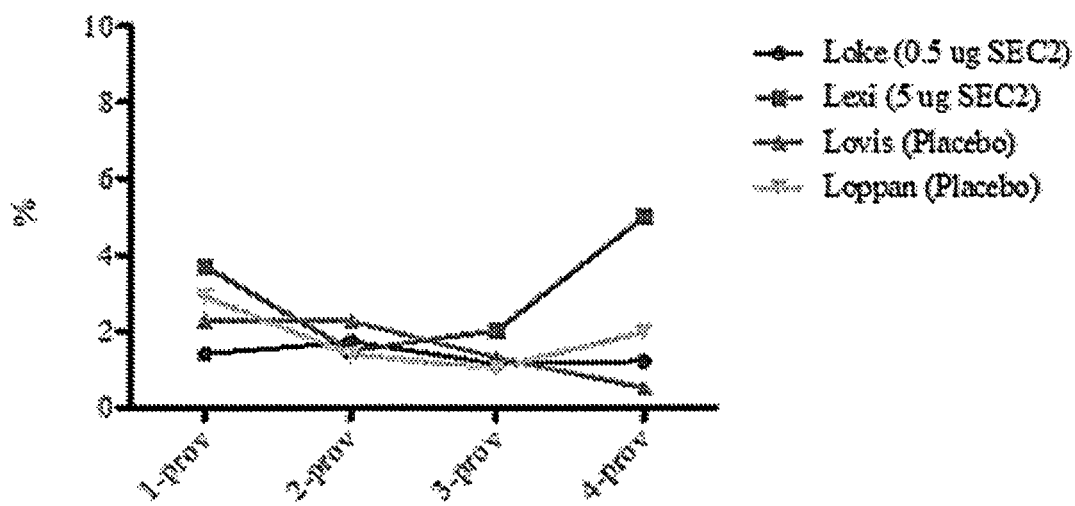
Figure 3B:
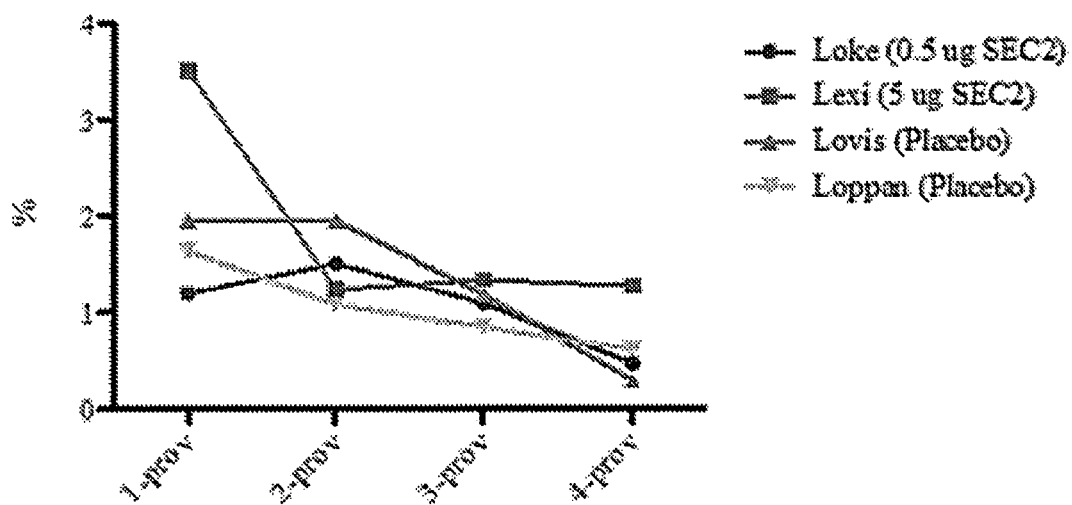

In both FIGS. 3A and 3B, one can see that the dog that received the higher dose of superantigen (Lexi, squares) has the highest proportion of FoxP3+, as well as Foxp3+CD25+ of the CD4-positive T-cells in the first sample ("1-prov") taken directly after the last dose of superantigen was administered. This can be interpreted as signs of strong activation of T-cells in this dog in response to the peroral superantigen treatment. Sample number 4 ("4-prov") was taken 3 weeks after the last dose of superantigen. Here one can see that the dog that received the highest dose of superantigen (Lexi, squares) has the highest proportion of FoxP3+ among blood lymphocytes. Similarly, this dog has the highest proportion of Foxp3+CD25+ among the CD4-positive blood T-cells 3 weeks after the last superantigen dose. Since the last sample was taken three weeks after the last dose of superantigen, the interpretation is that these cells represent regulatory T-cells, rather than activated "normal" T-cells, as the proportion of FoxP3+CD25+ decreased sharply during the same period of time among the other dogs.

Thus, neonatal treatment with superantigen results in a direct T-cell activation followed by an increase in putative regulatory T-cells, which thus could prevent adverse immune reaction such as allergies, inflammatory diseases and autoimmune diseases.

The invention claimed is:

1. A method for reducing the incidence of, or for prophylactic treating, an inflammatory disorder in a domestic non-human mammals, wherein the domestic animal is a dog, a cat, or a horse, the method comprising administering a pharmaceutical composition comprising a bacterial superantigen to a mucous membrane of a newborn of said domestic non-human mammals.

2. The method according to claim 1, wherein the pharmaceutical composition comprises at least one strain of the *Staphylococcus aureus* producing enterotoxin.

3. The method according to claim 1, wherein the pharmaceutical composition comprises at least one of the *Staphylococcus aureus* enterotoxins A, B, C1, C2, C3, D, E, G or H, enterotoxin-like toxins Q, M or K, or toxic shock syndrome toxin (TSST)-1.

4. The method according to claim 1, wherein the pharmaceutical composition comprises at least one streptococcal strain producing superantigen.

5. The method according to claim 1, wherein the pharmaceutical composition comprises at least one streptococcal superantigen.

6. The method according to claim 5, wherein said streptococcal superantigen is a streptococcal pyrogenic exotoxin, a streptococcal mitogenic exotoxin, or streptococcal superantigen A.

7. The method according to claim 3, wherein the superantigen in the pharmaceutical composition is *Staphylococcus aureus* enterotoxin C1, C2 or C3.

8. The method according to claim 7, wherein the superantigen in the pharmaceutical composition is *Staphylococcus aureus* enterotoxin C2.

9. The method according to claim 1, wherein the pharmaceutical composition is administered onto the intestinal mucous membrane of said newborn domestic non-human mammal.

10. The method according to claim 1, wherein the pharmaceutical composition is administered onto the nasal mucous membrane of said newborn domestic non-human mammal, or onto mucous membrane in the oral cavity of said newborn domestic non-human mammal.

11. The method according to any of the claim 1, wherein the pharmaceutical composition is administered to the newborn domestic non-human mammals within 3 months after birth.

12. The method according to claim 1, wherein the pharmaceutical composition is administered multiply.

13. The method according to claim 1, wherein the inflammatory disorder is an allergy.

14. The method according to claim 13, wherein the allergy is food allergy or atopic dermatitis.

15. The method according to claim 1, wherein the inflammatory disorder is an inflammatory disease.

16. The method according to claim 1, wherein the inflammatory disorder is an autoimmune disease.

17. The method according to claim 1, wherein the domestic animal is a dog or a cat.

18. The method according to claim 17, wherein the domestic animal is a dog.

19. The method according to claim 11, wherein the pharmaceutical composition is administered to the newborn domestic non-human mammal within 2 weeks after birth.

20. The method according to claim 19, wherein the pharmaceutical composition is administered to the newborn domestic non-human mammal within 10 days after birth.

21. The method according to claim 20, wherein the pharmaceutical composition is administered to the newborn domestic non-human mammal within 7 days after birth.

\* \* \* \* \*